(12) United States Patent
Parker et al.

(10) Patent No.: US 6,788,863 B2
(45) Date of Patent: Sep. 7, 2004

(54) OPTICAL DELAY DEVICE

(75) Inventors: Gregory J. Parker, Hampshire (GB); Martin Charlton, Southampton (GB); Majd Zoorob, Southampton (GB)

(73) Assignee: Mesophotonics Limited, Southampton (GB)

( * ) Notice: Subject to any disclaimer, the term of this patent is extended or adjusted under 35 U.S.C. 154(b) by 68 days.

(21) Appl. No.: 10/147,328

(22) Filed: May 17, 2002

(65) Prior Publication Data

US 2003/0002773 A1 Jan. 2, 2003

Related U.S. Application Data

(63) Continuation-in-part of application No. 09/910,014, filed on Jul. 23, 2001, now Pat. No. 6,640,034, which is a continuation of application No. 09/663,443, filed on Sep. 15, 2000, now abandoned, which is a continuation of application No. 09/415,233, filed on Oct. 12, 1999, now abandoned, which is a continuation of application No. PCT/GB98/01429, filed on May 18, 1998.

(30) Foreign Application Priority Data

May 16, 1997 (GB) .............................................. 9710062

(51) Int. Cl.[7] .............................. G02B 6/04; H04J 14/04
(52) U.S. Cl. ......................... 385/122; 385/27; 385/28; 385/24; 385/15; 385/129; 385/130; 385/141; 398/53; 398/44
(58) Field of Search ........................... 385/1, 2, 24, 14, 385/129, 130, 131, 132, 122, 141, 27, 28; 398/51, 53, 54, 44

(56) References Cited

U.S. PATENT DOCUMENTS

| | | | |
|---|---|---|---|
| 5,526,449 A | 6/1996 | Meade et al. | 385/122 |
| 5,651,079 A | 7/1997 | Goorjian | 385/16 |
| 5,682,401 A | 10/1997 | Joannopoulos et al. | 372/96 |
| 5,748,057 A | 5/1998 | De Los Santos | 385/134 |
| 5,751,466 A | 5/1998 | Dowling et al. | 359/248 |
| 5,802,236 A | 9/1998 | DiGiovanni et al. | 385/127 |
| 5,963,683 A | 10/1999 | Goorjian | 385/16 |
| 5,973,823 A | 10/1999 | Koops et al. | 359/322 |
| 5,978,530 A | 11/1999 | Russell et al. | 385/37 |

(List continued on next page.)

FOREIGN PATENT DOCUMENTS

| | | | | |
|---|---|---|---|---|
| EP | 0 836 112 A2 | 4/1998 | | 385/122 X |
| EP | 0123456 A2 | 1/2000 | | 385/14 X |
| EP | 1 024 378 A2 | 8/2000 | | 385/24 X |
| EP | 1 168 008 A2 | 1/2002 | | 385/122 X |
| EP | 1 205 788 A1 | 5/2002 | | 385/122 X |
| WO | 94/16345 A | 7/1994 | | 385/14 X |
| WO | WO 02/14913 A1 | 2/2002 | | 385/131 X |
| WO | WO 02/25781 A2 | 3/2002 | | 385/122 X |

OTHER PUBLICATIONS

Parker et al., "Optical Delay Device", U.S. patent application Publication No. U.S. 2003/0002773A1, published Jan. 2, 2003.*

(List continued on next page.)

*Primary Examiner*—Brian M. Healy
(74) *Attorney, Agent, or Firm*—Nixon & Vanderhye P.C.

(57) ABSTRACT

An optical device is provided comprising a delay region having a photonic band structure, an optical input, an optical output, wherein the optical input is adapted to couple input optical signals into a predetermined mode in the delay region such that the optical signal is slowed and wherein the optical output includes a wavelength selective element.

Input optical signals are coupled into a highly dispersive mode in the delay region in which the group velocity of the optical signal is reduced. The input signal, which has been delayed and dispersed, is recovered at the output of the device using the wavelength selective element.

32 Claims, 10 Drawing Sheets

U.S. PATENT DOCUMENTS

| | | | | |
|---|---|---|---|---|
| 5,987,208 | A | | 11/1999 | Gruning et al. ............. 385/146 |
| 6,002,522 | A | * | 12/1999 | Todori et al. ................ 359/573 |
| 6,028,693 | A | | 2/2000 | Fork et al. ................... 359/248 |
| 6,134,043 | A | | 10/2000 | Johnson et al. ............. 359/132 |
| 6,134,369 | A | | 10/2000 | Kurosawa ................... 385/132 |
| 6,175,671 | B1 | | 1/2001 | Roberts ....................... 385/14 |
| 6,278,105 | B1 | | 8/2001 | Mattia ..................... 250/214.1 |
| 6,310,991 | B1 | | 10/2001 | Koops et al. ................. 385/14 |
| 6,334,017 | B1 | | 12/2001 | West ........................... 385/123 |
| 6,343,167 | B1 | * | 1/2002 | Scalora et al. ................ 385/37 |
| 6,640,034 | B1 | * | 10/2003 | Charlton et al. ............ 385/122 |
| 2002/0021878 | A1 | | 2/2002 | Allan et al. ............. 385/129 X |
| 2003/0002773 | A1 | * | 1/2003 | Parker et al. ................. 385/15 |
| 2003/0118306 | A1 | * | 6/2003 | Deliwala .................... 385/125 |
| 2003/0228096 | A1 | * | 12/2003 | Parker et al. ................. 385/27 |

OTHER PUBLICATIONS

Kosaka et al, "Photonic Crystals for Micro Lightwave Circuits Using Wavelength–Dependent Angular Beam Steering" *Applied Physics Letters*, vol. 74, No. 10, Mar. 1999, pp. 1370–1372.

Agio et al, "Impurity Modes in a Two–Dimensional Photonic Crystal: Coupling Efficiency and Q Factor" *J. Opt. Soc. Am*, vol. 17, No. 12, Dec. 2000, pp. 2037–2042.

Kosaka et al, "Superprism Phenomena in Photonic Crystals: Toward Microscale Lightwave Circuits" *Journal of Lightwave Technology*, vol. 17, No. 11, Nov. 1999.

Mogilevtsev et al, "Group–Velocity Dispersion in Photonic Crystal Fibers" *Optics Letters*, vol. 23, No. 21, Nov. 1998, pp. 1662–1664.

O'Brien et al, "Lasers Incorporating 2D Photonic Bandgap Mirrors" *Electronics Letters*, vol. 32, No. 24, Nov. 1996.

Lee et al, "Microcavities, Photonic Bandgaps and Applications to Laser and Optical Communications" IEEE, 1999.

Kosaka et al, "Superprism Phenomena in Photonic Crystals" *Physical Review B*, vol. 58, No. 16, Oct. 1998.

Hosomi et al, "A Dispersion Compensator Using Coupled Defects in a Photonic Crystal" *IEEE Journal of Quantum Electronics*, vol. 38, No. 7, Jul. 2002, pp. 825–829.

Meltz et al, "Bragg Gating Formation and Germanosilicate Fiber Photosensitivity" International Workshop on Photoinduced Self–Organization Effects in Optical Fiber, SPIE vol. 1516, Oct. 1991, pp. 185–199.

Gaponenko et al, "Spontaneous Emission of Dye Molecules, Semiconductor Nanocrystals, and Rare–Earth Ions in Opal–Based Photonic Crystals" *Journal of Lightwave Technology*, vol. 17, No. 11, Nov. 1999, pp. 2128–2137.

Benisty et al, "Radiation Losses of Waveguide–Based Two–Dimensional Photonic Crystals: Positive Role of the Substrate" *Applied Physics Letters*, vol. 76, No. 5, Jan. 2000, pp. 532–534.

Koops et al, "Two–Dimensional Photonic Crystals Produced by Additive Nanolithography with Electron Beam–Induced Deposition Act as Filters in the Infrared" *Microelectronic Engineering*, 57–58, 2001, pp. 995–1001.

Krauss et al, "Photonic Crystals in the Optical Regime—Past, Present and Future" *Progress in Quantum Electronics*, vol. 23, 1999, pp. 51–96.

Cao et al, "Microlaser Made of Disordered Media" *Applied Physics Letters*, vol. 76, No. 21, May 2000, pp. 2997–2999.

Jin et al, "Band Gap and Wave Guiding Effect in a Quasi-periodic Photonic Crystal" *Applied Physics Letter*, vol. 75, No. 13, Sep. 1999, pp. 1848–1850.

XP–002226009, "466/OFC 2002/Thursday Morning" Mar. 2002, pp. 466–468.

Krauss et al, "Optical Characterization of Waveguide Based. . . ," vol. 68, No. 12, pp. 1613–1615 (1996).

* cited by examiner

OPTICAL DELAY DEVICE

This application is a continuation-in-part of application Ser. No. 09/910,014, filed Jul. 23, 2001, now U.S. Pat. No. 6,640,034, which is a continuation of Ser. No. 09/663,443, filed Sep. 15, 2000, now abandoned which is a continuation of Ser. No. 09/415,233, filed Oct. 12, 1999, now abandoned which is a continuation of PCT/GB98/01429, filed May 18, 1998, the entire content of which is hereby incorporated by reference in this application.

FIELD OF THE INVENTION

The present invention relates to the field of optical signal processing using photonic structures and in particular to optical signal delay elements.

BACKGROUND TO THE INVENTION

Periodic dielectric structures have been fabricated which exhibit photonic properties analogous in many respects to the electronic properties of semiconductors. A periodic variation in refractive index can give rise to a photonic band structure in which only certain photonic states are allowed This is most easily observed in the formation of a photonic band gap Structures exhibiting a photonic band gap forbid the transmission of light in a particular range of frequencies. Structures of this sort are disclosed in WO94/16345 and WO98/53351.

Photonic bandgap (PBG) structures can be formed by a slab of dielectric material having a periodic array of regions having a different refractive index. Holes can be drilled or etched into the material, or an array of columns can be formed Alternatively, stacks of dielectric material of alternating refractive index or a series of slots cut into a dielectric substrate can be used to form a 1-dimensional photonic crystal. The properties of the band structure are determined by the properties of the material and by the geometry of the structure.

Examples of the applications of photonic band structures include the formation of waveguides, use in lasing devices, sensors and even in optical multiplexers and demultiplexers.

SUMMARY OF THE INVENTION

According to one aspect of the invention an optical device comprises a delay region having a photonic band structure, an optical input, an optical output, wherein the optical input is adapted to couple an input optical signal of a particular wavelength into a predetermined mode in the delay region such that the optical signal is slowed, and, wherein the optical output includes a wavelength selective element to select said particular wavelength.

Input optical signals are coupled into a highly dispersive mode in the delay region in which the group velocity of the optical signal is reduced. The input signal, which has been delayed and dispersed, is recovered at the output of the device using the wavelength selective element Input signals comprising components of different wavelength can be used and each wavelength selected at the output.

Without a wavelength selective element the optical output is extremely distorted The highly dispersive nature of the delay region spreads the frequency content of an input optical signal and it is not possible to determine that any part of the signal has been delayed. The processing performed by the wavelength selective element results in the realisation of a delayed output.

The wavelength selective element may select wavelength spatially or temporally. Wavelength selection may be achieved by a wavelength selective element separate from the delay region or by a wavelength selection mechanism in which wavelengths are separated within the delay region. In the latter case, the wavelength selective element in the optical output is a correctly positioned output waveguide. Spatial wavelength selection may be achieved through mechanisms such as filtering, refraction, diffraction and interference. Temporal wavelength selection takes advantage of the fact that different wavelengths undergo a different delay The output signal can be gated to separate different wavelengths.

Preferably, the delay region comprises a first material having a first refractive index including an array of regions having a second refractive index. Preferably, the array extends over a plane in two dimensions. Alternatively, the delay region may be a 1-dimensional photonic crystal formed from a stack of dielectric slabs with alternate slabs forming the array of regions having a second refractive index, or a series of slots cut into a substrate material The array of regions having a second refractive index gives rise to a photonic band structure. The characteristics of the band structure are dependent on the geometry and material properties of the array of regions The frequency response of the delay region is therefore dependent on the geometry and material properties of the array of regions.

Preferably, the array has a low order of symmetry In particular, the order of rotational symmetry about a point in the array is preferably less than four A lower order of symmetry gives rise to a less uniform band structure, i.e. a more rapid variation of frequency with wave vector. This gives rise to a greater rate of change of group velocity around the band edges.

Preferably, the array of regions includes one or more defects This allows the band structure to be tuned more easily as it gives rise to a high Q-factor for the array The defect could, for example, be a missing region in the array, a displaced region or an enlarged or reduced region within the array. Alternatively, it could be a region within the array having a different refractive index to the rest of the array.

Preferably, the defect is formed from a superposition of two arrays. The superposition of lattices results in a Moire type structure which responds in a similar manner to a set of defects introduced into a single array and is easier to design. Having a set of defects allows light to be coupled into a defect mode more easily than for a single defect. Furthermore, having a large number of defects introduces flat bands in the band structure which allows greater optical delays to be achieved more readily.

Preferably, the first material is silicon nitride or silicon oxynitride.

The delay region may be adapted to allow the transmission of optical signals therethrough, but preferably is adapted to predominantly reflect optical signals of a particular wavelength of operation.

The frequency response of the delay region may be tuned by varying the temperature of the delay region. This causes expansion or contraction of the delay region and hence alters the geometry of the array. Alternatively a piezoelectric material could be used.

Alternatively, the frequency response of the delay region may be tuned by altering the refractive index structure of the delay region. This can be achieved by changing the material composition of the regions, for example when the array of regions is formed from an array of holes in a slab of material, the composition of the material filling the holes can be varied It can also be achieved by forming either the first material or the array of regions from an opto-electric material and applying a potential difference across the delay region.

The direction of incidence of optical signals relative to the array can be altered to obtain a different frequency response from the delay region. Preferably, this is achieved by rotation of the delay region relative to the optical input and optical output.

Preferably, the optical device is adapted to cause optical signals from the input to undergo multiple passes of the delay region. The greater the optical path length within the delay region the greater the delay on the optical signal.

The optical device may be adapted such that an input optical signal undergoes a plurality of passes through a delay region The optical device may also include multiple delay regions Input optical signals would then pass through each delay region in turn at least once.

Preferably, the optical device includes a delay region and waveguides, the waveguides causing multiple passes of input optical signals through the delay region.

More preferably, the optical device includes two delay regions arranged parallel to one another, each adapted to reflect the input optical signals toward the other, such that, in use, input optical signals undergo a plurality of reflections before reaching an optical output. Preferably, waveguides are positioned between the two delay regions to receive the reflected signals. The delay regions may be stacks of dielectric slabs of alternating refractive index arranged parallel to one another.

The wavelength selective device may be a simple optical filter.

The optical device may be adapted so that the delay region diffracts optical signals as well as slowing them. The optical output or outputs can then be placed at particular angular positions to receive particular orders of diffraction. The use of a diffracted beam as an output signal provides automatic wavelength selection. The delay region thus acts as the wavelength selective element. This combined functionality is achieved by matching the effective grating pitch of the delay region to the wavelength of operation whilst also coupling the input signals into a suitable mode.

The optical input may be arranged at an angle to an input or output facet of the delay region such that the input optical signal is refracted Owing to the dispersive nature of the delay region, different wavelengths travel at different speeds within it and hence will refract through different angles Therefore, by positioning the optical output to receive light refracted at a particular angle, wavelength selection is achieved. With the input at an angle to the input facet of the delay region the input optical signal is refracted at the input facet to spatially separate different wavelengths at the output facet. With the input normal to input facet but at an angle to the output facet the signal is refracted at the output to angularly separate different wavelengths at the output facet.

The optical device may form part of a phase-arrayed waveguide grating. The delay region is positioned in an input star coupler or a Multi-Mode Interference (MMI) region whilst the waveguides in a Mach-Zender type arrangement form the wavelength selective element.

Alternatively, the wavelength selective element may be an optical gate adapted to sample an optical output at different times. The sampling rate is dependent on the bit rate of the input optical signal.

According to a second aspect of the present invention, an optical device comprising a delay region having a photonic band structure, an optical input and an optical output, wherein the optical input is adapted to couple an input optical signal of a particular wavelength into a particular mode in the delay region such that the optical signal is slowed; and, wherein the delay region is adapted to predominantly reflect the input optical signal at the particular wavelength of operation to allow the input signal to be coupled into a highly dispersive mode.

According to a third aspect of the present invention, an optical device comprising a delay region having a photonic band structure, an optical input and an optical output, wherein the optical input is adapted to couple input optical signals into a particular mode in the delay region such that the optical signal is slowed; and, wherein the optical device is adapted to cause the optical signals from the input to undergo a plurality of passes through the delay region to thereby increase the optical path length of optical signals in the delay region.

The optical device may include two delay regions arranged parallel to one another, each adapted to reflect the input optical signals toward the other, such that, in use, input optical signals undergo a plurality of reflections before reaching an optical output.

According to a fourth aspect of the present invention a method of applying a delay to an optical signal comprises the steps of:

coupling the optical signal into a particular mode in a photonic band structure; and, selecting a part of the optical signal output from the photonic band structure, the selection being made on the basis of wavelength.

BRIEF DESCRIPTION OF THE DRAWINGS

Examples of optical devices in accordance with the present invention will now be described in detail with reference to the accompanying drawings, in which:

FIG. 9c shows an optimised design for the device of FIG. 9a;

FIG. 10b is a plot of time delay versus frequency for the device of FIG. 10a,

DETAILED DESCRIPTION

A brief summary of the considerations to be taken into account and the parameters that can be altered in a photonic crystal structure will first be given, followed by a detailed description of particular devices and designs in accordance with the invention.

Figure 1:
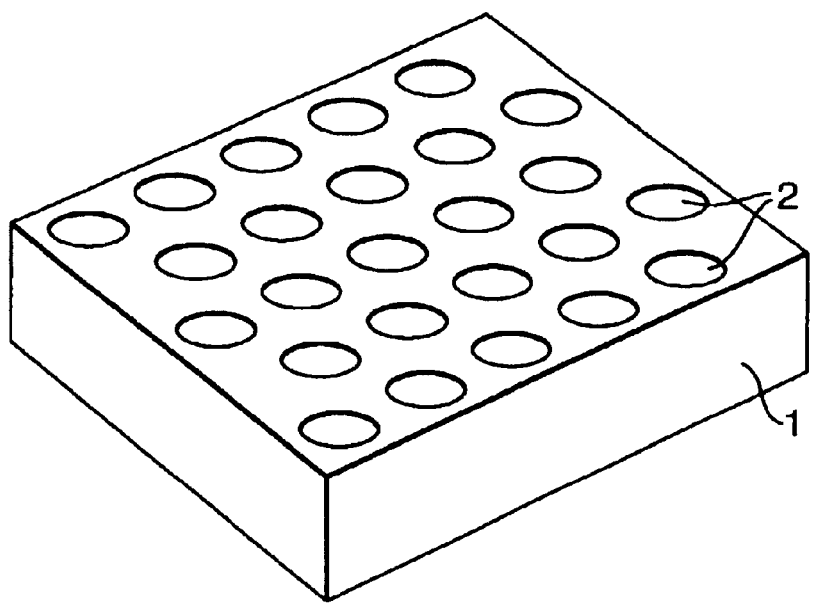
FIG. 1 shows a slab of dielectric material in which a lattice of air holes has been formed.
Figure 2:
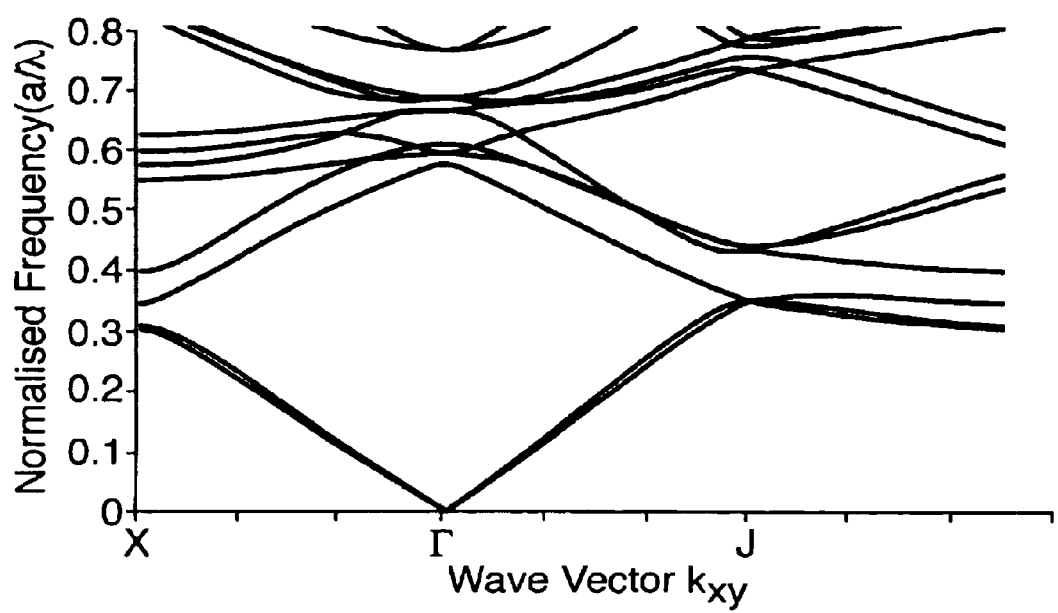
FIG. 2 is a plane wave band diagram for a silicon nitride structure having a lattice of air rods formed therein.

FIG. 1 shows a slab of dielectric material 1 in which a lattice of air holes 2 has been formed, suitable for use as a delay region in an optical delay element. The dielectric material is silicon nitride The refractive index contrast between the dielectric slab and the air holes must be sufficient to create a band structure. However, it is not necessary to create a complete band gap for the present invention and so relatively low index materials such as silicon nitride and silicon oxynitride can be used. The air holes 2 may be drilled into the slab but advantageously are etched. The array of air holes 2 gives rise to a photonic band structure as shown in FIG. 2. It is known how to fabricate structures of this type using drilling or etching.

FIG. 2 is a plane wave band diagram for the silicon nitride structure described above. The vertical axis is frequency and the horizontal axis is wave vector The band structure shows that the delay element is highly dispersive, especially close to photonic bandgap/pseudo bandgap edges. The gradient of the lines on the band diagram determines the group velocity while the absolute value of $\omega/\kappa$ determines the phase velocity. Therefore the group velocity of light at those specific frequencies close to the band edges is greatly reduced and may be zero if they optimally reach a point of inflection.

As stated above, it is not necessary to have a complete bandgap to obtain strong deviations in the group velocity. All that is required is that the frequency of operation of the delay is tuned to a specific band that is highly dispersive. Selecting a specific direction of propagation for the optical signal, for example the $\Gamma$X direction, provides an extra degree of freedom as partial bandgaps specific to the direction of propagation can be achieved.

Figure 3:
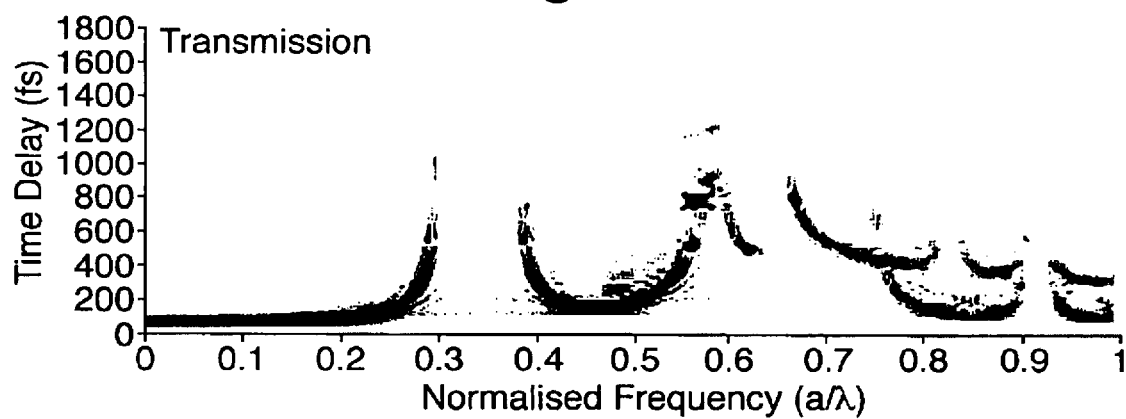
FIG. 3 is a plot of frequency versus time delay for a delay region formed from a slab of silicon nitride including an array of holes arranged in a triangular lattice structure, having 500 rows.

FIG. 3 is a plot of normalised frequency versus time delay for a delay region formed from a slab of silicon nitride including an array of holes arranged in a triangular lattice structure, having 500 rows The optical signal is propagated along the $\Gamma$X direction. The results are obtained using a Finite-Difference Time Domain (FDTD) technique. The broadband light emerging from the photonic crystal material is collected and the frequency content is calculated with respect to time. This post-processing is necessary to filter the severe chirping effects arising from the dispersion. Similar post-processing will be described in more detail in relation to functional delay devices below.

The x-axis indicates the normalised frequency, which is scaled to the lattice pitch of the structure. The normalised frequency is equal to $a/\lambda$ where a is the pitch of the lattice and $\lambda$ is the wavelength of light. The y-axis indicates the relative time of arrival of different frequencies. The time scale does not give any indication of the absolute time of travel of the different frequencies through the structure. As can be seen, close to the band edges the time of arrival increases dramatically. However the intensity of these signals are weaker owing to the difficulty in coupling into the modes close to the band edges A point of inflection on the band diagram giving zero group velocity is difficult to realise in reality as it lies just inside a band gap and so signals are not able to propagate through the structure.

It is clear that structures of this type can be used as dispersion compensators. If a suitable band is selected the dispersion of the structure can be used cancel the dispersion properties of an optical fibre The band structure can be tuned or optimised for a particular application through choice of appropriate geometry, material system, filling fraction, length and propagation direction.

The symmetry of a photonic crystal has a direct bearing on its band structure. The lower the symmetry of the crystal the greater the rate of change of group velocity with respect to frequency. This provides a means of varying the time delay of different frequencies simultaneously. This may be used, for example, in a dense wavelength division multiplexing (DWDM) application where many channels are equally spaced in wavelength. It has been found that a lattice structure having an order of symmetry of less than 4 is advantageous in practical applications, where the order of symmetry is the order of rotational symmetry about a lattice point.

The absolute length of the photonic crystal structure is very important in determining the amount of delay imparted to an optical signal. The length of the photonic crystal is directly related to the maximum attainable time delay. The time delay scales linearly with the number of rows of the structure and hence longer structures can be used to achieve longer time delays However longer structures give rise to greater losses.

The response of the delay region can be tuned by a variety of methods For example, heating the delay region causes expansion and hence an increase in the hole spacing This directly affects the frequency response of the delay region. Another way to tune the delay region is to form it from a piezoelectric material and apply a voltage across it. This has the same expansive or contractive effect as a variation in temperature and hence affects the frequency response of the delay region. Alternatively, an electro-optic material could be used which has a refractive index which is responsive to applied voltage. A further possibility is to select a material to fill the holes forming the sub-array to have a particular refractive index in order to obtain a desired response. This can be done permanently or can be done dynamically using a variable composition fluid to fill the holes.

The introduction of defects into the delay region also affects the photonic band structure. The addition of a set of defects introduces flat bands and allows light to be more easily coupled into particular dispersion modes in the delay region. Sets of defects of this sort can be formed from the superposition of two regular lattices to from a Moire pattern. The Moire pattern behaves like a set of defects in a regular lattice.

The direction of propagation of an optical signal in the photonic crystal is also crucial to its frequency response as well providing the possibility for additional effects such as diffraction. The example in FIG. 3 is taken along the $\Gamma$X direction, which in a triangular lattice provides a primary band gap with no diffraction, as the wavelength of operation of the band gap is large compared with effective grating pitch. Propagation in the [J direction in a triangular lattice introduces diffraction which can used to provide extra functionality In practical delay devices the delay region may be fixed with respect to the optical input and outputs or may be rotatable relative to the optical input and outputs to provide a variable response.

Figure 4:
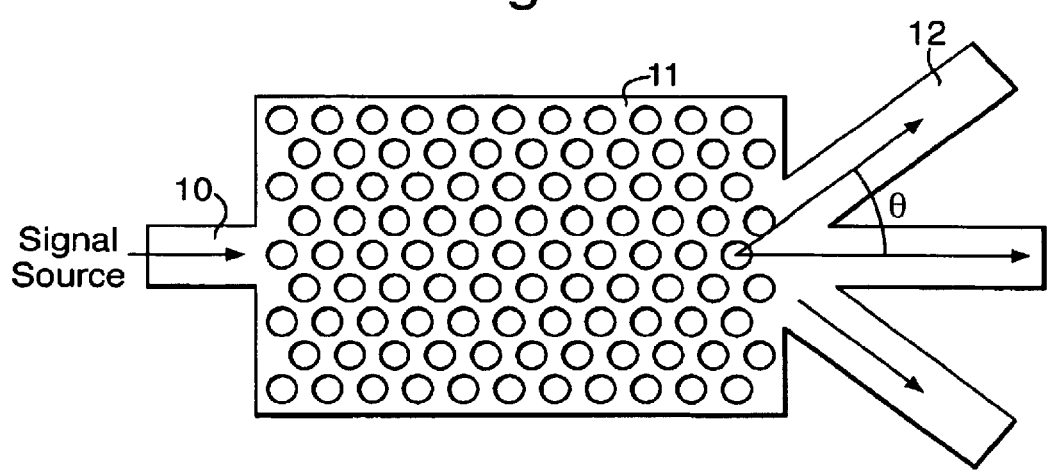
FIG. 4 is a schematic showing a delay device according to the present invention utilising diffraction.

The onset of diffraction could cause problems in time delay devices using the [J direction owing to ghosting and interference of the signal by the diffraction when many channels are processed in parallel Nevertheless, the first order diffraction can be used. The diffracted beams also experience a reduced group velocity and the use of a diffracted beam provides an automatic post-processing step The beam is diffracted at a specific angle The diffraction angle can be calculated and used as an output waveguide tilt angle. FIG. 4 shows a possible design for a device using this method. Optical signals enter the device at input 10 and pass through the delay region 11. The signals are both delayed and diffracted in the delay region 11. Optical output 12 is positioned to receive the first order diffracted beam.

Figure 5:
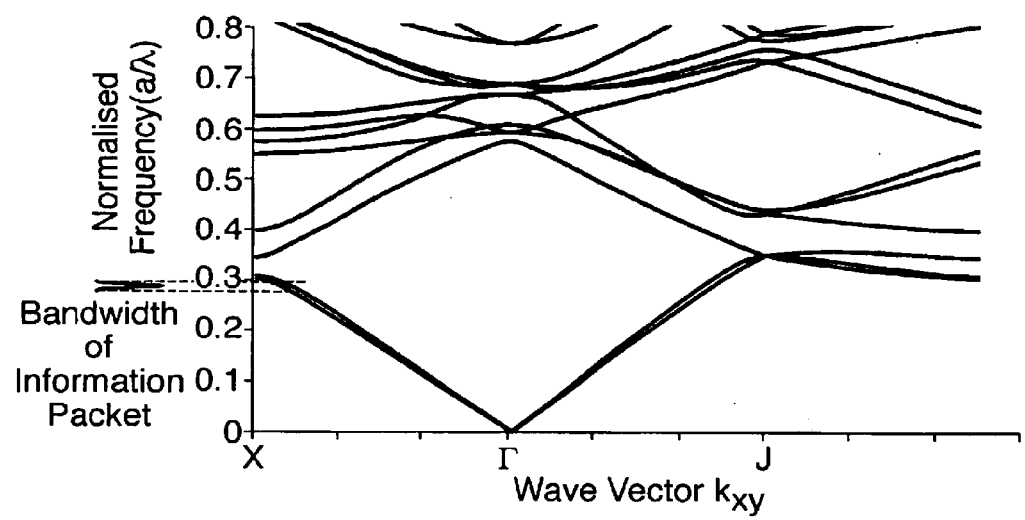
FIG. 5 is a band diagram showing the bandwidth of a packet of light carrying a single bit of information.
Figure 6:
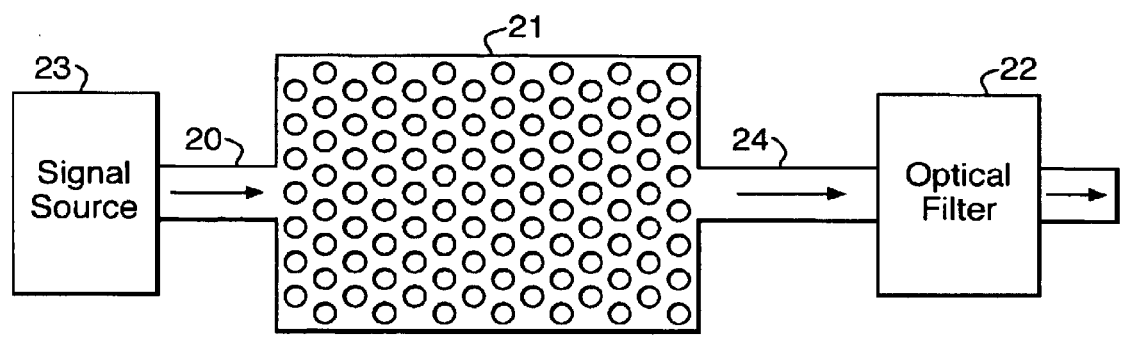
FIG. 6 illustrates a basic in-line delay device in accordance with the present invention.
Figure 7A:
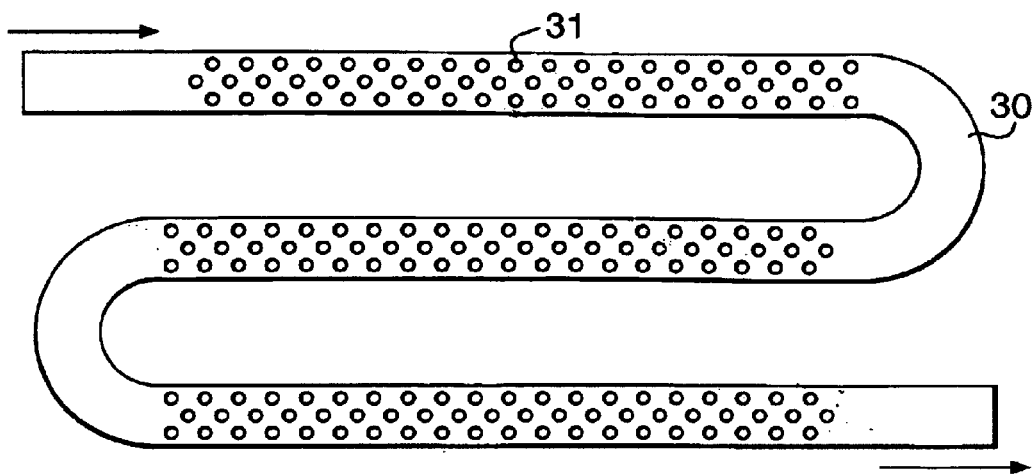
FIG. 7a illustrates an in-line device in accordance with the present invention comprising a bending waveguide including delay regions.

The use of photonic crystals having higher order of long range symmetry, such as quasi-crystals, allows an input signal to be split into many different signals using diffraction The bit rate of signals propagating through photonic crystal structures is critical to its usefulness. It is vital that the line width of each pulse must be much narrower than the variation in the dispersion band at that point otherwise the signal is severely distorted in shape and cannot be identified. This is illustrated in FIG. 5. The path length of the optical signal within the photonic crystal must be sufficient to provide an adequate time delay for the desired application. For relatively short time delays an in-line device may be suitable as is shown in FIG. 6. FIG. 6 shows schematically an optical input 20, a delay region 21 and a wavelength selective element 22 at the output. However for longer time delays that might be required for dispersion compensation in a fibre more complex designs can be used to keep the device compact. FIG. 7a shows a snaking waveguide 30 including regions of material 31 having a photonic band structure. The regions 31 are formed by an array of air holes in the waveguide material. The construction shown is such that the delay regions can be formed in a single slab with the waveguide 30 and waveguide bends subsequently formed. Input optical signals are constrained within the waveguide 30 and thus pass through the delay region a plurality of times to give a relatively long optical path length within the delay region. The waveguide 30 can be formed in a conventional manner as described in Optical Waveguide Theory, by Allan Snyder and J. D. Love, Chapman & Hall.

Figure 7B:
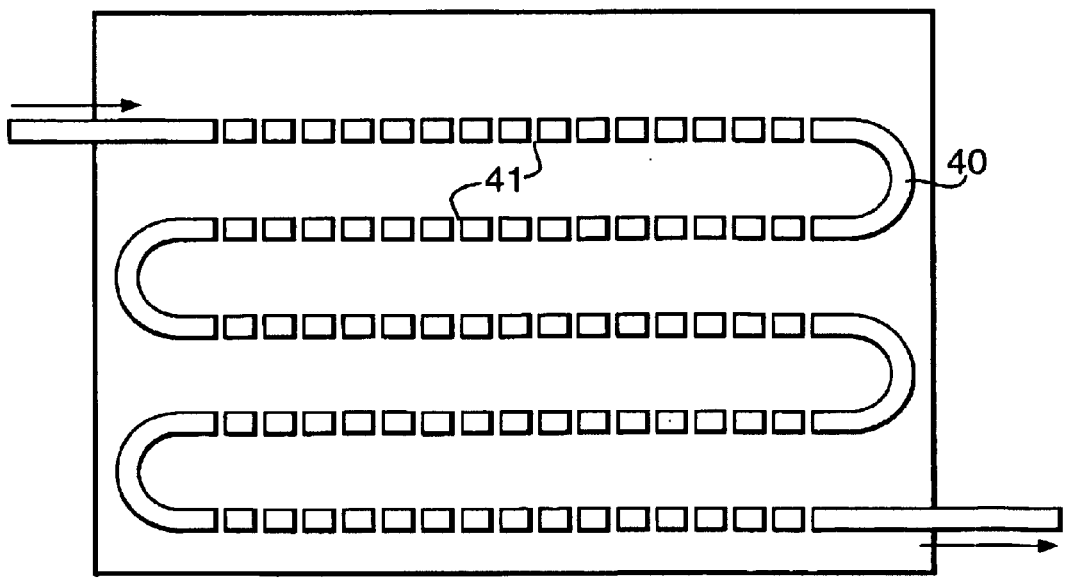
FIG. 7b illustrates a similar structure to FIG. 7a, wherein the delay regions are formed from slabs cut into the waveguide.

FIG. 7b shows a similar design with air channels 41 etched into a snaking waveguide 40. Alternative designs of the same type are possible. Very long path lengths in a small area can be obtained with a spiral design.

Figure 8:
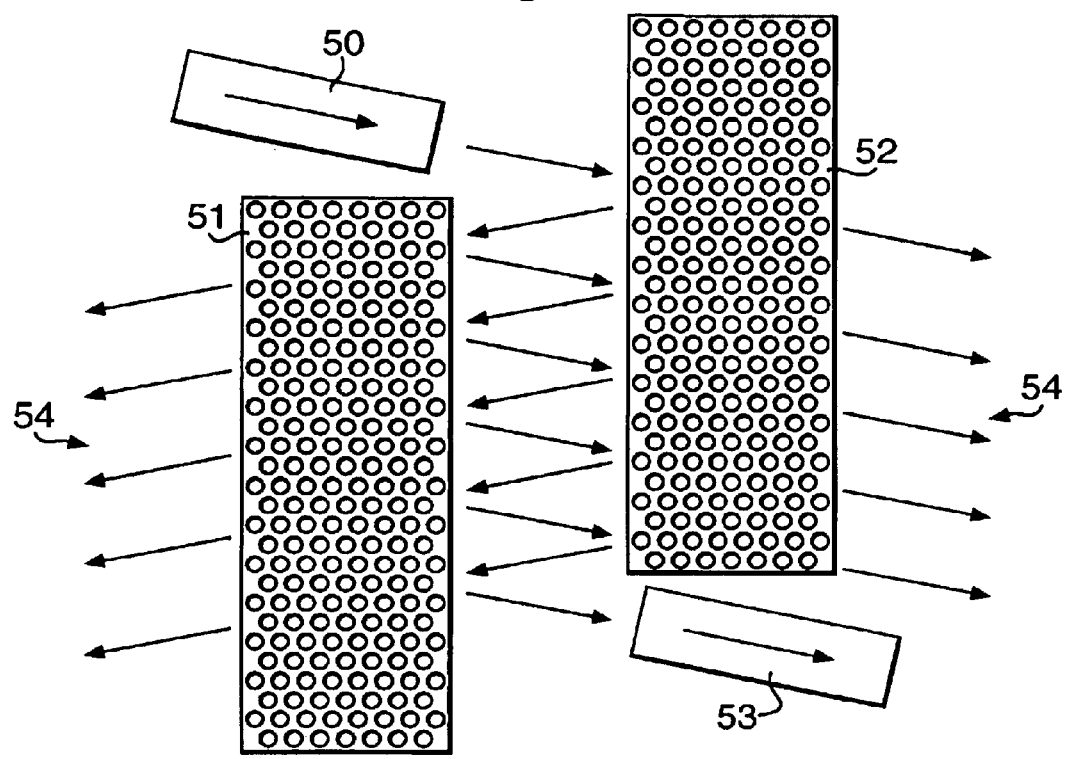
FIG. 8 shows an optical delay device according to the present invention using a reflection regime.
Figure 9A:
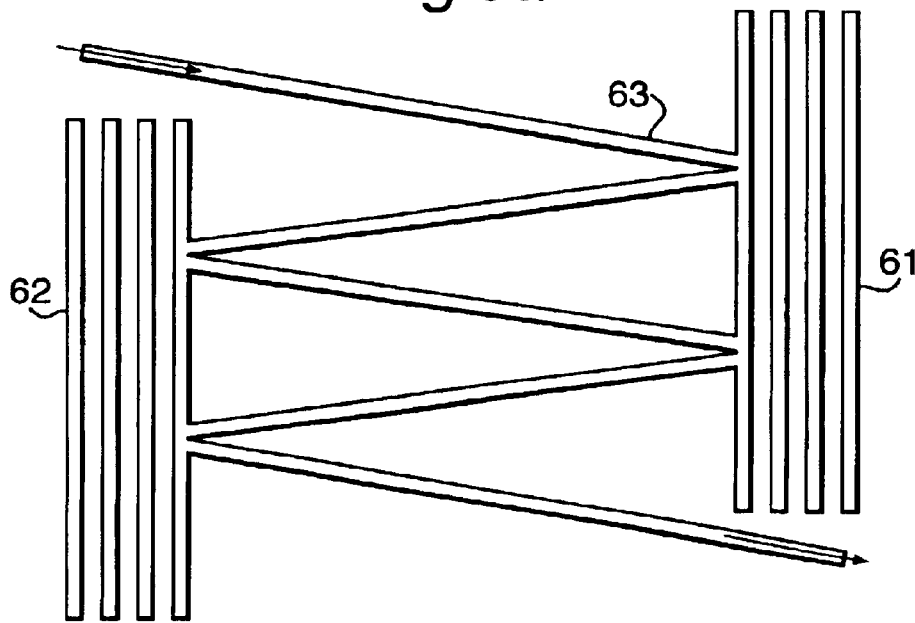
FIG. 9a shows a delay device using reflection, including waveguides between the two delay regions.
Figure 9B:
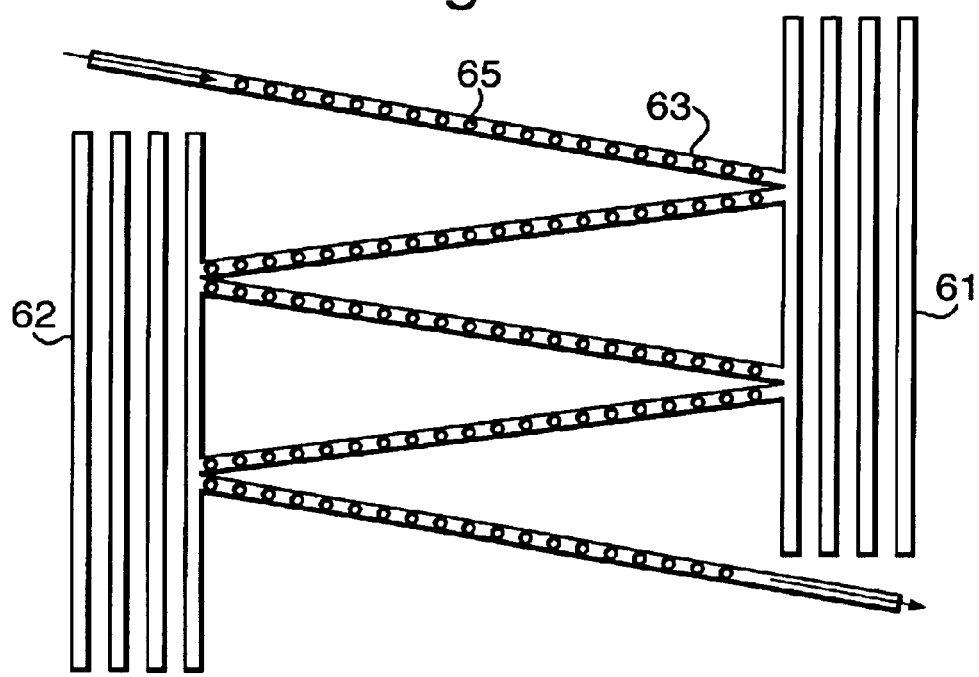
FIG. 9b shows a delay device similar in structure to the device of FIG. 9a but wherein the delay region is in the waveguides and the dielectric stacks are used for reflection.

In a reflection scheme greater delays can be achieved then in transmission for a given loss of signal strength. A photonic band structure can be used in an etalon type structure. This is shown in FIG. 8. Input optical signals are input at almost normal incidence to the delay regions 51,52 and undergo multiple reflections before reaching the output 53. The wavelength selective element is not shown. By using photonic band structures in a reflection regime it is possible to couple input optical signals into a mode closer to a band edge than in a transmission regime Close to a band edge transmission is attenuated severely. By contrast, tuning the input optical signals close to the band edge reduces losses due to multiple partial reflections in an etalon type structure. Thus it is possible to achieve a greater delay for a given path length in the delay region using a reflection regime and it is also possible to achieve a greater path length for a given loss FIG. 9a shows waveguides formed between two dielectric stacks 61,62 which are in effect 1-dimensional photonic crystals The difference in refractive index between adjacent layers of the stack is at least 10% The stacks 61,62 give rise to a band structure and so can be used to introduce a time delay. The waveguides 63 reduce loss which is a major problem owing to the number of reflections required to produce long time delays Alternatively the structure of the dielectric stacks can be designed to give nse to a band gap at the frequency of operation to provide reflection of an optical signal, whilst the intermediate waveguides provide the delay in a transmission regime. This is illustrated in FIG. 9b. Clearly optical delay could be provided both by the stacks in reflection and by delay regions in intermediate waveguides.

Figure 9C:
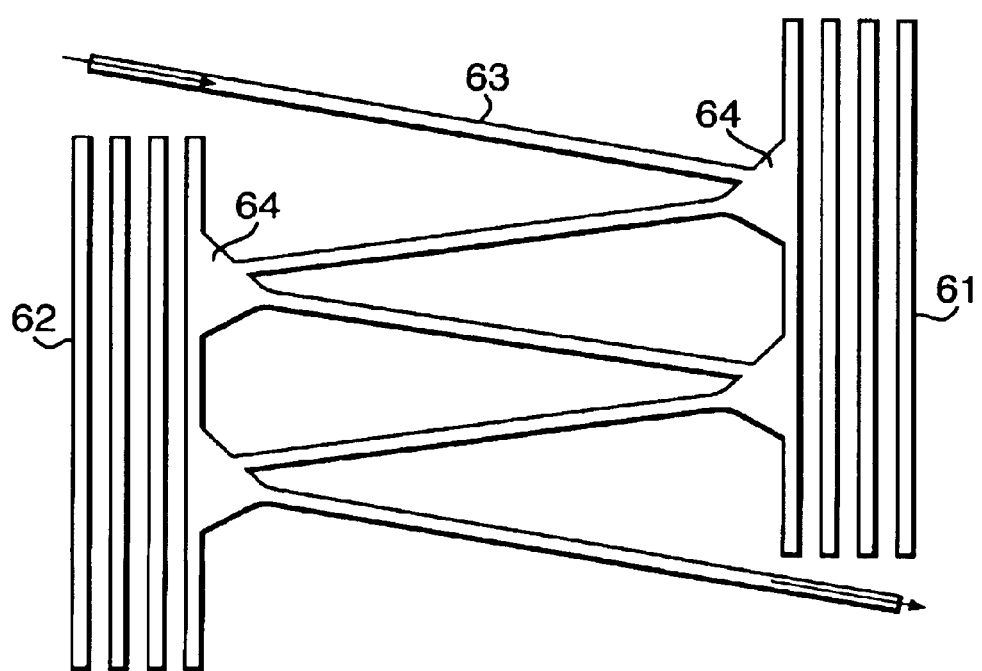

FIG. 9c shows an improved design for the device of FIG. 9a. Divergence spreads optical beams on incidence with the reflective stacks. The introduction of tapers 64 provides improved coupling into adjacent waveguides.

Figure 10A:
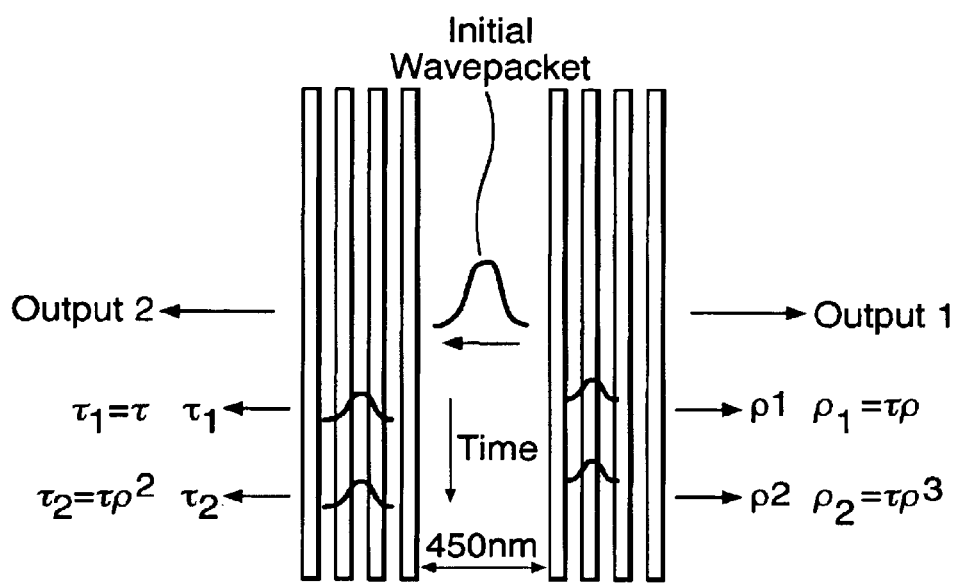
FIG. 10a illustrates the multiple outputs of a delay device using a reflection regime.
Figure 10B:
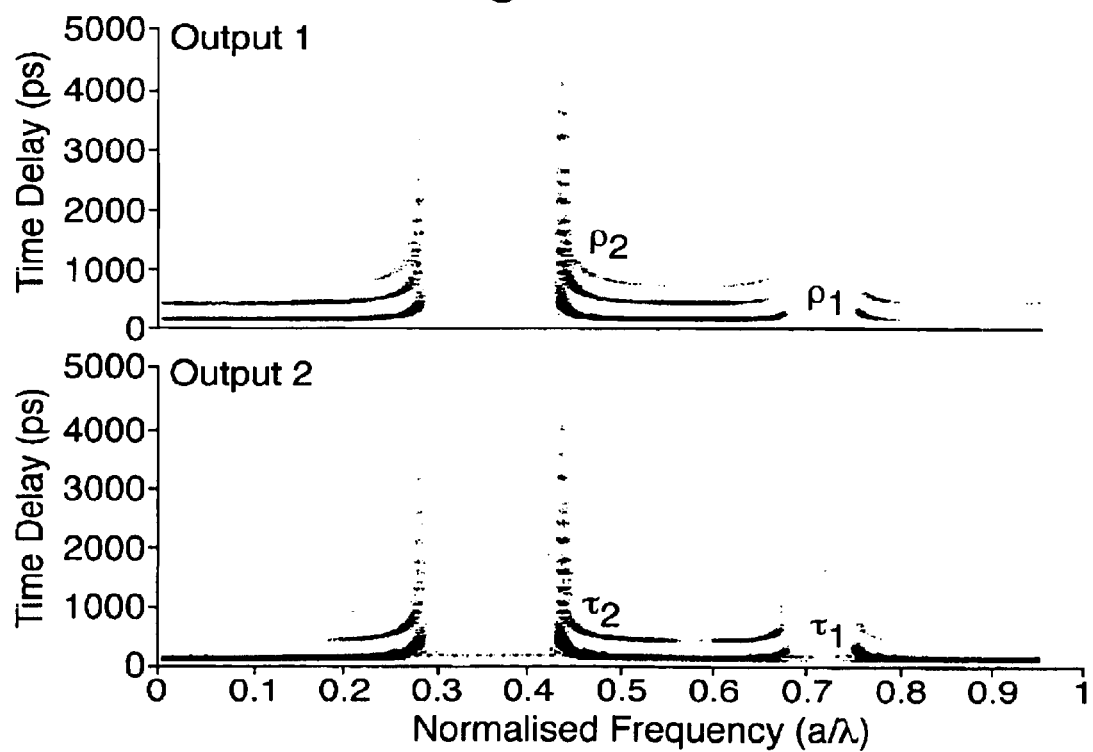

The structures of FIGS. 8 and 9 operate like an etalon in that for each reflection there will also be partial transmission. Thus there may be multiple output signals each with a different time delay. FIG. 10 illustrates the time delay for each signal and FIG. 10b is a plot showing the time delay versus frequency The reflective elements are dielectric stacks each having 100 rows. The dielectric used in silicon oxynitride The distance between the two stacks is set at 450 mm. As can be seen in FIG. 10b there is an increase in the time delay with each reflection but there is also an associated decrease in intensity of the optical signal. For this reason the use of intermediate waveguides is highly beneficial.

A time delay or dispersion compensation device using a photonic crystal as a highly dispersive region also requires a wavelength selective element at the output. A wavelength selective element is required in order to recover the input signal This post processing can be achieved in a number of ways.

FIG. 4 shows perhaps the simplest way to provide the necessary wavelength selection As described above, the input beam is both delayed and diffracted Correct positioning of an output waveguide 12 allows the first order diffraction beam to be used as the output. The diffracted beam is necessarily wavelength separated and so the processing is achieved integrally with the delay region.

Figure 11:
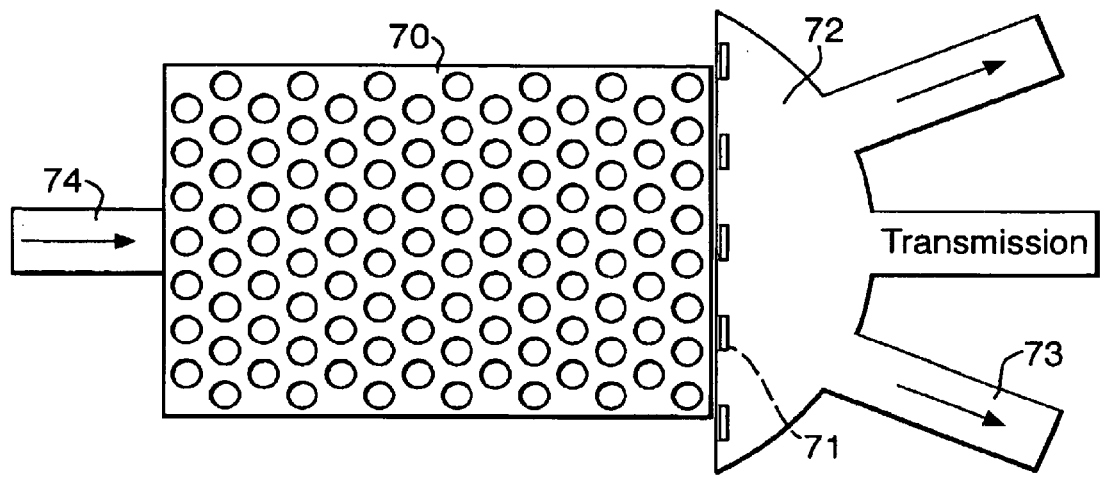
FIG. 11 shows an optical delay device according to the present invention including a diffraction grating at the optical output.

Alternatively, a transmission diffraction grating 71 can be incorporated at the output of the photonic band structure device 70 as illustrated in FIG. 11. This provides a method of selecting the correct frequency at the output The grating pitch may be tuned to the specific frequency of operation with a free-space region 72 to allow the diffracted beams to propagate into the output waveguides 73.

Figure 12A:
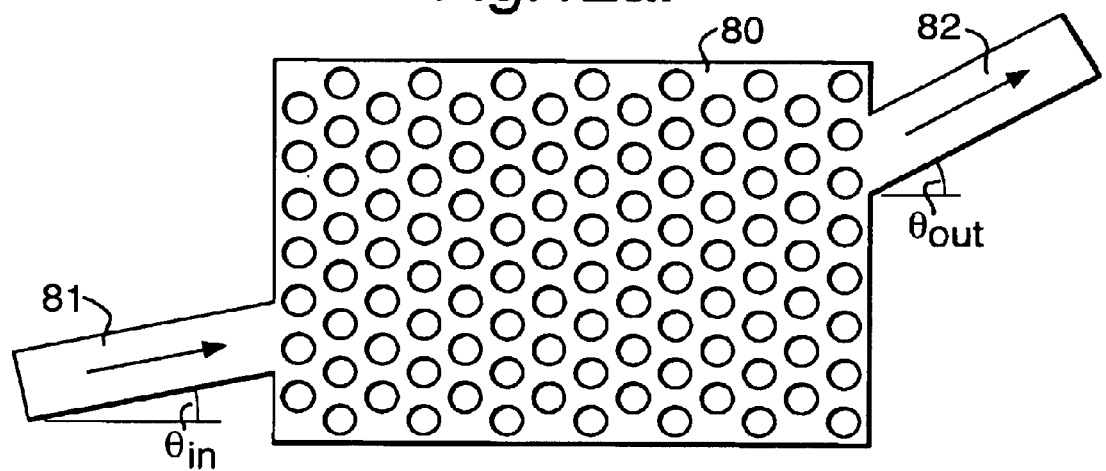
FIG. 12a shows an optical delay device according to the present invention using refraction to isolate the required wavelength.

A further alternative is shown in FIG. 12a and exploits the strong variations in the group velocity of the photonic band structure itself to refract the correct frequency to a specific angle. Owing to the large variations in group velocity around the desired region of operation a small incident angle fin provides a large refracted output angle $\theta_{out}$. This can provide very accurate frequency separation.

Figure 12B:
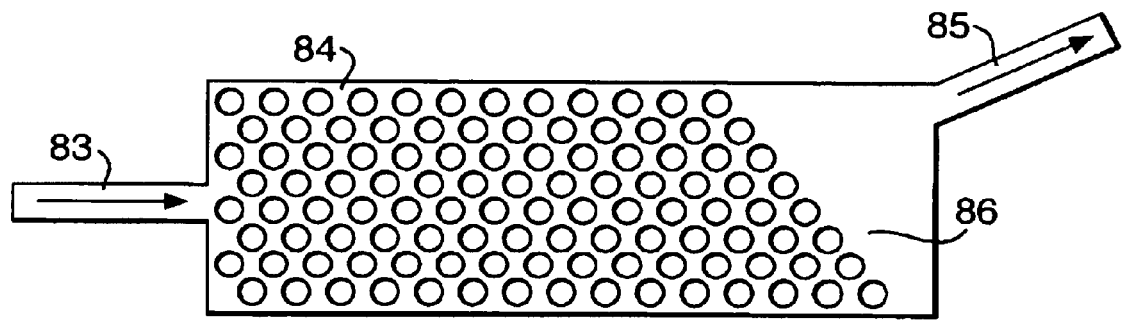
FIG. 12b shows an alternative to the device of FIG. 12a, FIG. 13 shows a phase-arrayed waveguide grating including a delay region in accordance with present invention, and, FIG. 14 is a schematic representation of an optical delay device including an optical gating device.

FIG. 12b shows a further example exploiting refraction. The output facet of the photonic crystal delay region 81 is angled. The output beam is refracted to varying degree in dependence on wavelength The output waveguide 82 is positioned to receive an output beam of the wavelength of operation.

Figure 13:
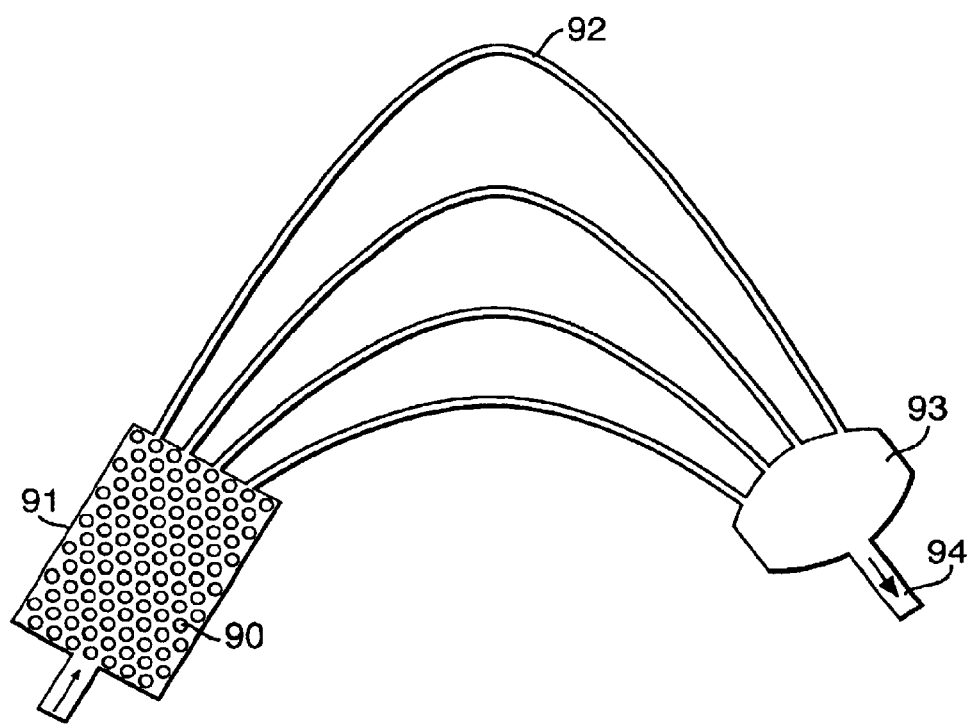

Another means for selection of the desired frequency is use of a phased-array waveguide grating as shown in FIG. 13. The delay region 90 having a photonic band structure is placed in a slab region of the input coupler 91. The optical signal is delayed and allowed to diverge in the delay region 90. The diverged light is coupled to the waveguides 92, which may include tapers to improve coupling efficiency. The number of waveguides and the phase difference introduced between them provides the device with the versatility to select the required frequency with the desired resolution. At the output, a free-space slab region 93 is placed so that light diffracted out of the phased array waveguide is efficiently coupled into the output waveguide 94, which is positioned at the correct location and exact tilt to couple the right frequency of light.

A further possibility is a simple optical filter.

Figure 14:
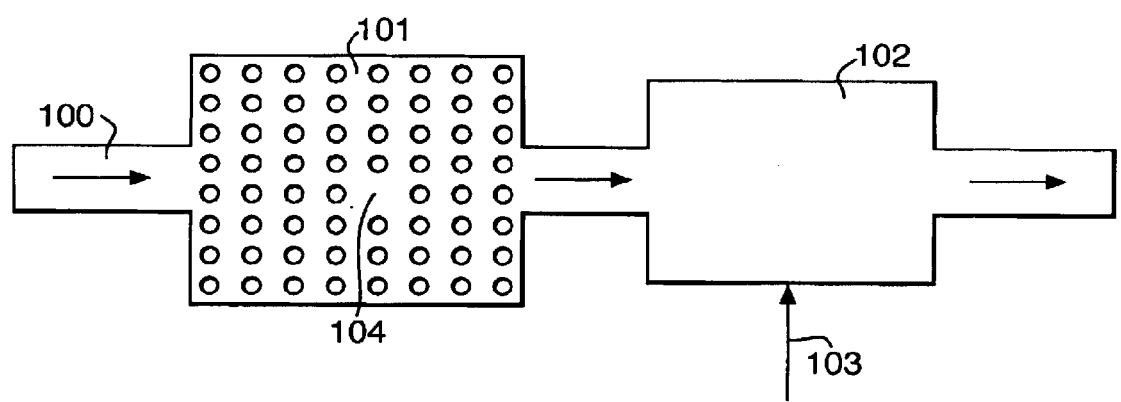

Another way to isolate the required wavelength is to sample the output at different times using an optical gating device, such as a Kerr cell Different wavelengths undergo different amounts of delay and so are separated in time at the output. The gating device 102 can be very simply attached at the output of the delay device as is shown schematically in FIG. 14. FIG. 14 shows an optical input 100, a delay region 101 and a Kerr Cell 102 which is controlled by an electrical control signal 103. The Kerr Cell acts as a shutter which is opened and closed in accordance with the electrical input signal 103.

The sampling rate is related to the bit rate of the input optical signal The bit rate in a telecoms network is usually set and so the gating device can be set up for the particular network it is in. However, the lower the bit rate the longer the intervals that can be sampled by the gating device and hence the greater the power that can be collected. Reducing the bit rate therefore provides lower loss for a given time delay, and conversely a longer time delay for a given loss. In fact, the time delays for a 1 Tbit network have been shown to be more than 10 times the time delays in a 14.1 Tbit network for the same power.

All of the above examples of wavelength selection are described with reference to transmission delay regions Clearly similar arrangements can be made with delay regions working in a reflection scheme using backward diffraction or a transmission wavelength selective element at the output.

There are a number of ways of tuning the time delay imparted to an input optical signal. For example the angle of incidence of the input optical beam relative to the structure of the delay region can be altered to alter the resultant time delay. The photonic crystal can be heated or cooled to tune the frequency response as the crystal expands or contracts. In a photonic crystal comprising an array of holes in a dielectric substrate, the holes of the photonic crystal structure may be filed with different substances or mixtures to alter their refractive index and thus alter the time delay imparted to an optical signal. The aspect ratio of the photonic crystal can also be altered to tune the time delay The aspect ratio is directly related to the rate of change of time delay with respect to frequency, i.e. the sharpness of the band structure.

In order to be able to tune the optical delay more sensitively a defect can be introduced into the photonic crystal structure. The defect gives the delay region a higher Q factor, making it more sensitive to the tuning measures described above.

What is claimed is:

1. An optical device comprising a delay region having a photonic band structure, an optical input and an optical output, wherein the optical input is adapted to couple an input optical signal of a particular wavelength into a particular mode in the delay region such that the optical signal is slowed; and, wherein the optical output includes a wavelength selective element to select said particular wavelength.

2. An optical device according to claim 1, wherein the delay region comprises a first material having a first refractive index including an array of regions having a second refractive index.

3. An optical device according to claim 2, wherein the array extends over a plane in two dimensions.

4. An optical device according to claim 2, wherein the delay region is a 1-dimensional photonic crystal formed from a stack of dielectric slabs, with alternate slabs forming the array of regions having a second refractive index, or from a series of slots in a dielectric substrate.

5. An optical device according to any claim 2, wherein the array has an order of rotational symmetry about a point in the array of less than four.

6. An optical device according to claim 2, wherein the array of regions includes one or more defects.

7. An optical device according to claim 6, wherein the defects are the result of a superposition of two arrays.

8. An optical device according to claim 2, wherein the first material is silicon nitride or silicon oxynitride.

9. An optical device according to claim 1, wherein the delay region is adapted to predominantly reflect optical signals of a particular wavelength of operation.

10. An optical device according to claim 1, wherein the frequency response of the delay region is tuned by varying the temperature of the delay region.

11. An optical device according to claim 1, wherein the frequency response of the delay region is tuned by forming at least part of the delay region from a piezoelectric material and applying a potential difference across the delay region.

12. An optical device according to claim 1, wherein the frequency response of the delay region is tuned by altering the refractive index structure of the delay region.

13. An optical device according to claim 12, wherein the array of regions is formed from an array of holes in a slab of material and the composition of the material filling the holes is selected to tune the frequency response of the delay region.

14. An optical device according to claim 12, wherein either the first material or the array of regions is formed from an opto-electric material and a potential difference is applied across the delay region to tune the frequency response of the delay region.

15. An optical device according to claim 1, wherein the direction of incidence of optical signals relative to the array can be altered to obtain a different frequency response from the delay region.

16. An optical device according to claim 15, wherein the delay region is adapted to be rotated relative to the optical input and optical output.

17. An optical device according to claim 1, wherein the optical device is adapted to cause optical signals from the input to undergo multiple passes of the delay region.

18. An optical device according to claim 1, adapted such that input optical signals undergo a plurality of passes through the delay region.

19. An optical device according to claim 18, wherein the optical device includes waveguides, the waveguides causing multiple passes of input optical signals through the delay region.

20. An optical device according to claim 1, including multiple delay regions.

21. An optical device according to claim 20, wherein the optical device includes two delay regions arranged parallel to one another, each adapted to reflect the input optical signals toward the other, such that, in use, input optical signals undergo a plurality of reflections before reaching an optical output.

22. An optical device according to claim 21, wherein waveguides are positioned between the two delay regions to receive the reflected signals.

23. An optical device according to claim 1, wherein the wavelength selective element is an optical filter.

24. An optical device according to claim 1, wherein the delay region diffracts optical signals as well as slowing them.

25. An optical device according to claim 24, wherein the optical output or outputs are placed at particular angular positions relative to the optical input to receive particular orders of diffraction.

26. An optical device according to claim 1, wherein the optical input is arranged at an angle to an input or output facet of the delay region such that the input optical signal is refracted.

27. An optical device according to claim 1, wherein the optical device is a phase-arrayed waveguide grating and the delay region is positioned in an input coupler and waveguides form the wavelength selective element.

28. An optical device according to claim 1, wherein the wavelength selective element is an optical gate adapted to sample an optical output at different times.

29. An optical device comprising a delay region having a photonic band structure, an optical input and an optical output, wherein the optical input is adapted to couple an input optical signal of a particular wavelength into a particular mode in the delay region such that the optical signal is slowed; and, wherein the delay region is adapted to predominantly reflect the input optical signal at the particular wavelength of operation to allow the input signal to be coupled into a highly dispersive mode.

30. An optical device comprising a delay region having a photonic band structure, an optical input and an optical output, wherein the optical input is adapted to couple input optical signals into a particular mode in the delay region such that the optical signal is slowed; and, wherein the optical device is adapted to cause the optical signals from the input to undergo a plurality of passes through the delay region to thereby increase the optical path length of optical signals in the delay region.

31. An optical device according to claim 30, wherein the optical device includes two delay regions arranged parallel to one another, each adapted to reflect the input optical signals toward the other, such that, in use, input optical signals undergo a plurality of reflections before reaching an optical output.

32. A method of applying a delay to an optical signal comprises the steps of:

coupling the optical signal into a particular mode in a photonic band structure; and, selecting a part of the optical signal output from the photonic band structure, the selection being made on the basis of wavelength.

* * * * *